(12) United States Patent
Pless et al.

(10) Patent No.: US 7,158,833 B2
(45) Date of Patent: *Jan. 2, 2007

(54) FERRULE FOR CRANIAL IMPLANT (75) Inventors: Benjamin D. Pless, Atherton, CA (US);
Dennis Potts, Scotts Valley, CA (US)

(73) Assignee: NeuroPace, Inc., Mountain View, CA (US)

( * ) Notice: Subject to any disclaimer, the term of this patent is extended or adjusted under 35 U.S.C. 154(b) by 512 days.

This patent is subject to a terminal disclaimer.

(21) Appl. No.: 10/639,842

(22) Filed: Aug. 12, 2003

(65) Prior Publication Data

US 2004/0034368 A1   Feb. 19, 2004

Related U.S. Application Data

(63) Continuation-in-part of application No. 09/724,936, filed on Nov. 28, 2000, now Pat. No. 6,618,623.

(51) Int. Cl.
*A61N 1/36* (2006.01)

(52) U.S. Cl. ............................. 607/45; 607/139

(58) Field of Classification Search ............... 607/45, 607/116
See application file for complete search history.

(56) References Cited

U.S. PATENT DOCUMENTS

| | | | |
|---|---|---|---|
| 3,444,861 A | 5/1969 | Schulte | |
| 4,328,813 A | 5/1982 | Ray | |
| 4,629,451 A | 12/1986 | Winters et al. | |
| 4,805,634 A | 2/1989 | Ullrich et al. | |
| 4,998,938 A | 3/1991 | Ghajar et al. | |
| 5,464,446 A | 11/1995 | Dreessen et al. | |
| 5,843,150 A | 12/1998 | Dreessen et al. | |
| 5,865,842 A | 2/1999 | Knuth et al. | |
| 5,927,277 A | 7/1999 | Baudino et al. | |
| 5,954,687 A | 9/1999 | Baudino | |
| 6,016,449 A | 1/2000 | Fischell et al. | |
| 6,018,094 A | 1/2000 | Fox | |
| 6,044,304 A | 3/2000 | Baudino | |
| 6,248,080 B1 | 6/2001 | Miesel et al. | |
| 6,427,086 B1 * | 7/2002 | Fischell et al. | 607/45 |
| 6,618,623 B1 * | 9/2003 | Pless et al. | 607/45 |
| 7,089,059 B1 * | 8/2006 | Pless | 607/45 |

FOREIGN PATENT DOCUMENTS

| | | |
|---|---|---|
| EP | 0 433 852 A1 | 6/1991 |
| EP | 0 433 852 B1 | 6/1991 |

OTHER PUBLICATIONS

U.S. Appl. No. 09/373,676, filed Aug. 13, 1999, Fischell et al.
U.S. Appl. No. 09/517,797, filed Mar. 2, 2000, David R. Fischell.

(Continued)

*Primary Examiner*—Carl Layno
(74) *Attorney, Agent, or Firm*—Morrison & Foerster LLP (57) ABSTRACT

A ferrule for removably retaining a self-contained implantable device within a cranial opening of a patient is set forth. The ferrule includes a shelf portion, a wall portion, and at least one supporting tab connected to the wall portion. The shelf portion has an inner surface and an outer surface. The inner surface of the shelf portion substantially conforms to an implantable device. The wall portion has an inner surface and an outer surface and encompasses the shelf portion. The inner surface of the wall portion substantially conforms to the implantable device and the outer surface of the wall portion substantially conforms to the cranial opening.

47 Claims, 6 Drawing Sheets

OTHER PUBLICATIONS

U.S. Appl. No. 09/543,264, filed Apr. 5, 2000, Benjamin D. Pless.
U.S. Appl. No. 09/543,450, filed Apr. 5, 2000, Benjamin D. Pless.
U.S. Appl. No. 09/557,168, filed Apr. 19, 2000, Fischell et al.
U.S. Appl. No. 09/609,086, filed Jun. 30, 2000, Fischell et al.
U.S. Appl. No. 09/706,322, filed Nov. 3, 2000, Pless.
U.S. Appl. No. 09/711,663, filed Nov. 9, 2000, David Greene.
U.S. Appl. No. 09/724,805, filed Nov. 28, 2000, Pless et al.

* cited by examiner

FERRULE FOR CRANIAL IMPLANT

CROSS REFERENCE TO RELATED APPLICATIONS

This application claims priority to and is a continuation-in-part of U.S. patent application Ser. No. 09/724,936, now U.S. Pat. No. 6,618,623, entitled, "Ferrule for Cranial Implant," which was filed on Nov. 28, 2000, the entirety of which is incorporated herein by reference.

FIELD OF THE INVENTION

This invention relates to an apparatus for removably retaining a self-contained implantable device within a cranial opening of a patient.

BACKGROUND

Systems for providing electrical stimulation of the brain are increasingly popular for the treatment of neurological disorders such as epilepsy or migraine headaches. A brain neurostimulator device may include a signal processor to detect the onset of a neurological event and a pulse generator for providing electrical stimuli to treat the neurological event. The neurostimulator device further includes one or more leads having one or more electrodes operatively connected to the brain. The neurostimulator device sends and receives electrical signals to and from the brain via the electrodes on the lead. Access to the brain is achieved by drilling a hole in the patient's skull. The lead is passed through the hole and positioned at the desired site or sites on or within the brain. The lead is typically secured to the skull by an anchoring system and the signal processor and pulse generator portions of the neurostimulator device generally reside outside the patient's cranium.

Although the signal processing and pulse generator portions of neurostimulator devices are often not implanted in the cranium, many functional and aesthetic advantages can be gained in doing so. For example, as can be appreciated, many opportunities exist for traction on the portion of the lead that is positioned outside the skull in systems where the signal processing and pulse generator portions of neurostimulator devices reside outside the cranium. In such systems, the leads need to be tunneled along the neck and down the pectoral region where the neurostimulator resides, for example, as in the Medtronic Activa® device of Medtronic, Inc., Minneapolis, Minn. Such an implementation subjects the leads to fatigue. Any accidental tug on the lead outside of the skull could result in movement of the portion of the lead positioned within the skull. If the lead is accidentally moved such that the electrodes are also dislocated from their sites, the continued proper functioning of the neurostimulator device would require invasive repositioning of the electrodes. In current designs, the success of preventing the lead from being moved depends upon the effectiveness of the lead anchoring system. Implanting the neurostimulator within the cranium of the patient would help reduce traction on the leads.

One example of an implantable system is disclosed in U.S. Pat. No. 6,016,449 entitled "System for Treatment of Neurological Disorders" issued to Fischell, et al. on Jan. 18, 2000 (hereinafter "Fischell"). Fischell discloses a responsive detection and stimulation system for the early recognition and prompt treatment of a neurological event arising from neurological disorders such as epilepsy, migraine headaches, and Parkinson's disease. In Fischell, the entire implantable portion of the system for treating neurological disorders lies under the patient's scalp. By placing the entire system within the cranium, as opposed to having some wires extending into or through the neck to a control module in the chest, the probability of wire breakage due to repeated wire bending is drastically reduced. Other examples of devices implanted in the cranium for applying electrical stimulation therapies to electrodes sited at appropriate locations include cochlear implants.

Implantation of a neurostimulator device into the skull is complicated by a number of factors. For example, implantation requires surgical removal of a portion of the cranium that is generally larger than that required for the implantation of anchoring systems for securing a lead alone. Further, skull dimensions, contours and thicknesses vary from patient to patient. Nevertheless, a standard-shaped device is desirable, as is a relatively low-cost means for adapting a standard-shaped device to the confines of the cranial opening unique to each patient.

One solution, proposed in this patent, for adapting an implantable device to the confines of the cranial opening is a ferrule. The ferrule, which is secured to the cranium, is designed to receive and secure a neurostimulator device. The ferrule has an inner shape that is adapted for receiving and securing neurostimulator devices and an outer shape that substantially conforms to the unique cranial opening of the patient. In essence, the ferrule helps de-couple the device shape from the shape of the cranial opening.

Additional functional demands of the ferrule include supporting and preventing the neurostimulator device from severely impinging on the brain as a result of impact to the device. Also, the neurostimulator device must be secured to the ferrule to prevent its accidental dislocation, yet allow for its removal or access for maintenance or the replacement of the battery or device. Furthermore, the ferrule must be adequately secured to the cranium of the patient and aesthetically blend with the exterior contour of the skull. The present invention is directed to satisfying these needs.

SUMMARY

In accordance with one aspect of the present invention, there is provided a ferrule for removably retaining a self-contained implantable device within a cranial opening created in a patient for that purpose. The ferrule includes a shelf portion having an inner surface and an outer surface. The inner surface of the shelf portion substantially conforms to an implantable device. The ferrule further includes a wall portion that encompasses the shelf portion. The wall portion has an inner surface and an outer surface. The inner surface of the wall portion substantially conforms to an implantable device and the outer surface substantially conforms to the cranial opening of the patient. The ferrule also includes at least one supporting feature, possibly a tab, connected to the wall portion.

There is also provided a method for removably retaining a self-contained implantable device within a cranial opening of a patient. The method includes forming an opening in the cranium of the patient and providing a ferrule. The ferrule includes a shelf portion having an inner surface and an outer surface. The inner surface of the shelf portion substantially conforms to an implantable device. The ferrule further includes a wall portion that encompasses the shelf portion. The wall portion has an inner surface and an outer surface. The inner surface of the wall portion substantially conforms to an implantable device and the outer surface substantially conforms to the cranial opening of the patient. The ferrule also includes at least one supporting feature, possibly a tab, connected to the wall portion. The ferrule is inserted into the cranial opening and fixed to the cranium. Then an implantable device is inserted into the ferrule and secured thereto.

BRIEF DESCRIPTION OF THE DRAWINGS

The foregoing and other advantages of the invention will become apparent upon reading the following detailed description and upon reference to the drawings in which.

While the invention is susceptible to various modifications and alternative forms, specific variations have been shown by way of example in the drawings and will be described herein. However, it should be understood that the invention is not limited to the particular forms disclosed. Rather, the invention is to cover all modifications, equivalents, and alternatives falling within the spirit and scope of the invention as defined by the appended claims.

DETAILED DESCRIPTION OF THE INVENTION

Turning now to the drawings, FIGS. 1–5 illustrate a ferrule 100 for removably retaining a self-contained implantable device 101 within a cranial opening of the patient. Having a self-contained implantable device, which is removable, may help facilitate total device replacement. That is, with a self-contained implantable device, all the device components may be in a single device housing, which is then hermetically sealed. In this way, the device seal need not be violated. In addition, the potential risk of user infection and risk of device damage may be minimized. The ferrule 100 includes a wall portion 102, a shelf portion 104, a rim 106, at least one supporting tab 108, and a retainer 109 for securing implantable device 101 within the ferrule.

Figure 2:
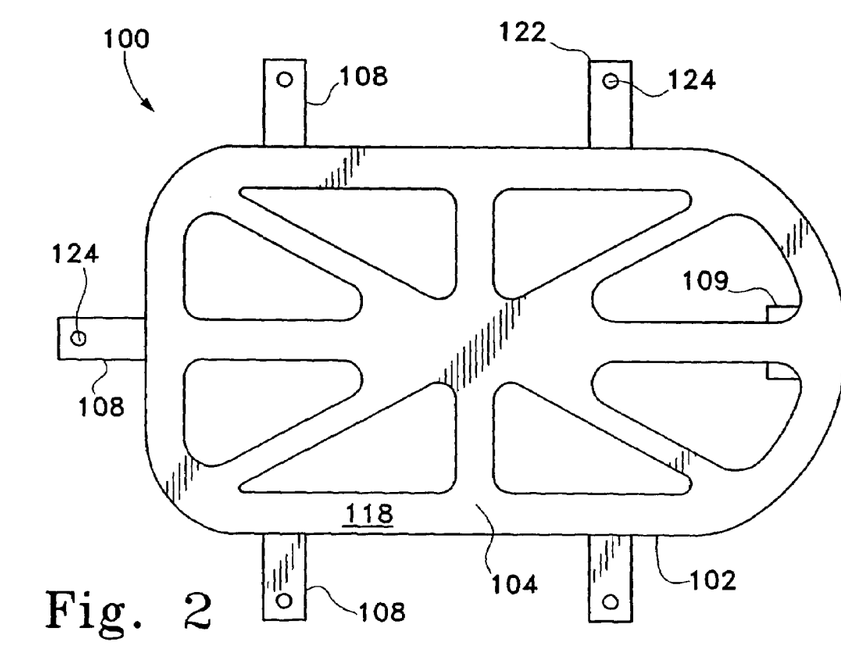
FIG. 2 is a bottom view of the ferrule of the present invention.

The wall portion 102 encompasses and extends upwardly from the shelf portion 104. The wall portion 102 includes an outer surface 110 and an inner surface 112. The shelf portion 104 extends inwardly from the inner surface 112 of the wall portion 102 and defines an aperture 114. However, the invention is not so limited and an aperture 114 need not be defined in the shelf portion 104. The shelf portion 104 may be any shape and define a plurality of apertures, for example, as shown in FIG. 2. The shelf portion 104 includes an inner surface 116 and an outer surface 118. The shelf portion 104 supports the self-contained implantable device 101 on the inner surface 116.

The rim 106 encompasses the wall portion 102 and is interrupted by the upwardly extending supporting tabs 108. Each of the supporting tabs 108 includes a proximal end 120 and a distal end 122. The supporting tab 108 is connected to the wall portion 102 relatively near the proximal end 120 and an aperture 124 for receiving a bone screw is defined relatively near the distal end 122.

Figure 1:
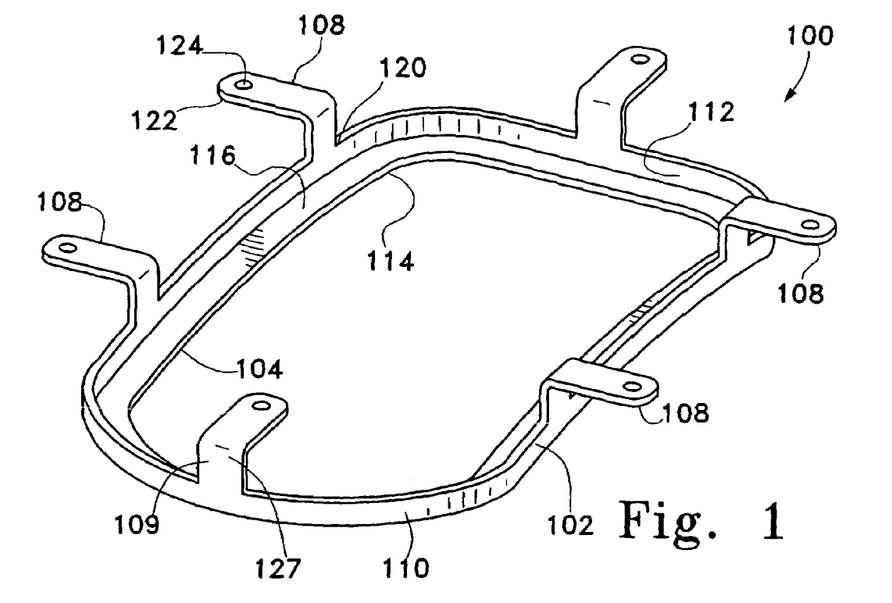
FIG. 1 is a perspective view of the ferrule of the present invention having an elongated shape.
Figure 3:
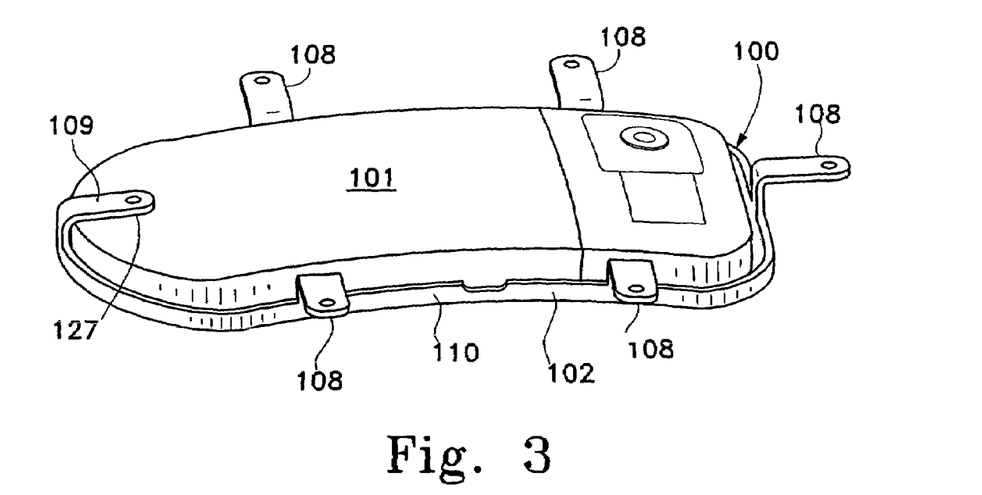
FIG. 3 is a perspective view of the ferrule of the present invention having an elongated shape with an implantable device.
Figure 4:
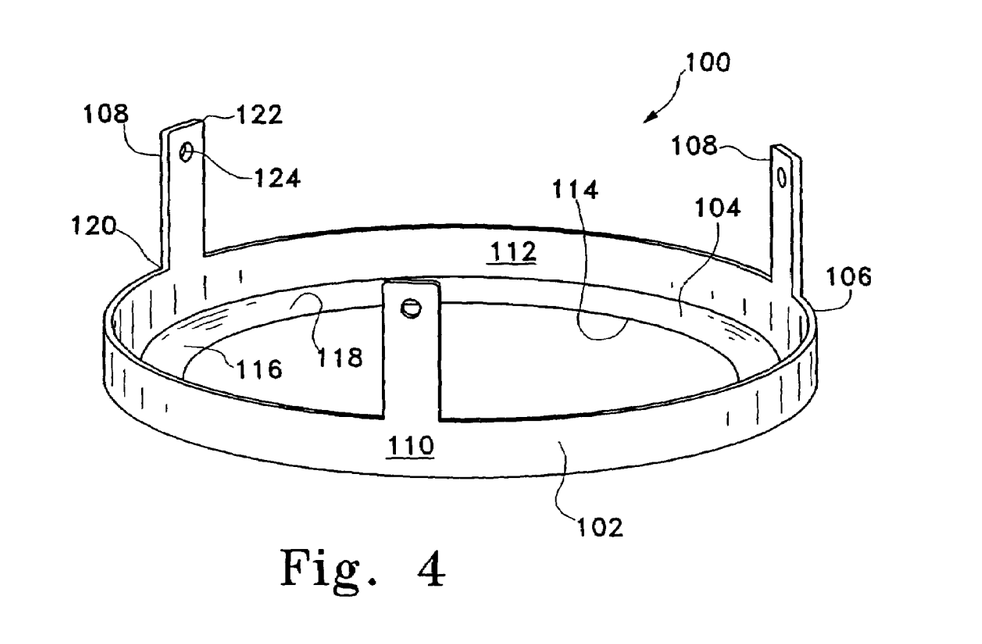
FIG. 4 is a perspective view of the ferrule according to one variation of the present invention.
Figure 5:
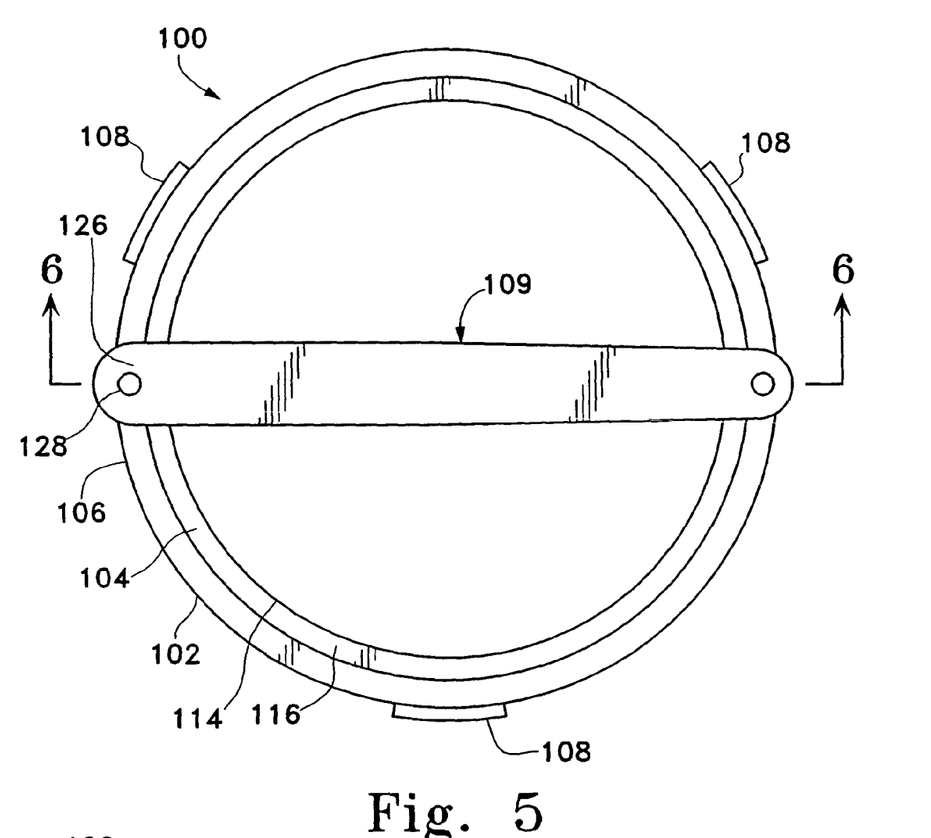
FIG. 5 is top view of the ferrule according to one variation of the present invention.

As shown in FIGS. 1–3, the ferrule 100 is substantially elongated in shape to receive an implantable device 101 that is similarly elongated in shape. However, the invention is not so limited. For example, as shown in FIGS. 4 and 5 the wall portion 102 is generally annular in shape and encompasses an annular-shaped shelf portion 104. The aperture 114 defined by the shelf portion 104 is circular and centrally located. However, the wall portion 102, shelf portion 104, and the aperture 114 may be of any shape. Furthermore, the shapes may be de-coupled from one another. For example, the outer surface 110 of the wall portion 102 may be elliptical in shape, the inner surface 112 of the wall portion 102 may define a polygon, and the aperture 114 may be circular and not centrally located. Generally, the ferrule 100 has an outer shape that conforms to the cranial opening and an inner shape that is suitable for receiving the self contained implantable device 101.

One retainer 109 for removably retaining self-contained implantable device 101 is shown in FIGS. 1 and 3. The retainer 109 includes a detent portion 127 extending generally upwardly and inwardly from the wall potion 102. The implantable device 101 is removably retained within the ferrule 100 between the detent portion 127 and the shelf portion 104. Although only one detent portion 127 is shown, additional detent portions 127 may be incorporated within the scope of the invention. The detent portions 127 may be bent into position prior to or upon insertion of the implantable device 101. Also, the detent portion 127 may be utilized in combination with another retainer 109, such as with sutures (not shown) to secure the implantable device 101.

Figure 6:
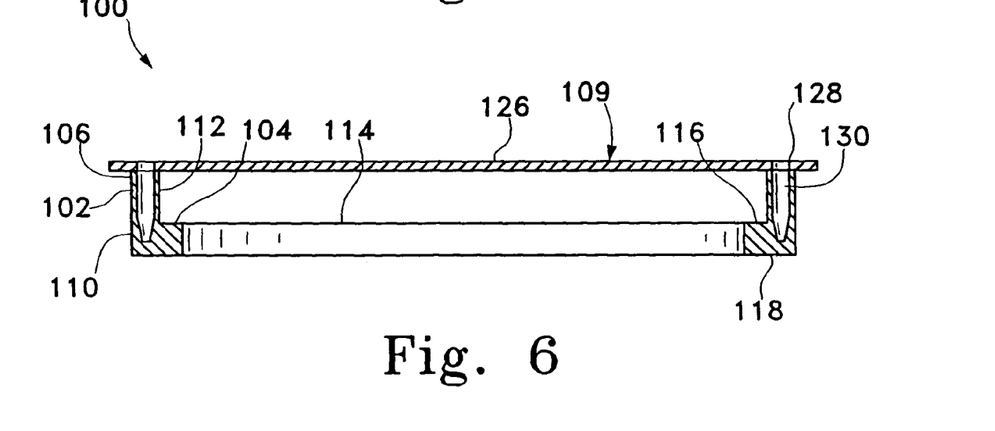
FIG. 6 is a cross-sectional view along line 6—6 of FIG. 5 of the ferrule of the present invention.

Another retainer 109 for removably retaining a self-contained implantable device 101 is shown in FIGS. 5 and 6. The retainer 109 includes a locking member 126. The locking member 126 defines at least one aperture 128 and the wall portion 102 of the ferrule 100 defines at least one corresponding receiving bore 130 adapted for securing the locking member 126 to the wall portion 102. The receiving bore 130, for example, may be threaded for receiving a screw or adapted for receiving a rivet. The aperture 128 of the locking member 126 is aligned with the receiving bore 130 of the wall portion 102 and is secured thereto with a screw being passed through the aperture 128 in the locking member 126 and into the receiving bore 130 of the wall portion 102.

Although FIGS. 5 and 6 show the locking member 126 defining two apertures 128 and the wall portion 102 defining two receiving bores 130, the invention is not so limited and the number of apertures 128 and corresponding bores 130 may be varied to optimize performance. Additional apertures 128 and receiving bores 130 may be employed to secure the locking member 126 to the wall portion 102. Also, additional apertures in the locking member 126 and receiving bores in the implantable device 101 may be employed to secure the locking member 126 to the self-contained implantable device 101 in addition to securing the locking member 126 to the wall portion 102 of the ferrule 100.

Furthermore, although an elongated locking member 126 is shown, the locking member 126 may be of any shape. The locking member 126 may have a shape generally corresponding to the shape of the wall portion 102. For example, if the wall portion 102 is elliptical, the locking member 126 may also be elliptical. Multiple locking members 126 are also within the scope of the invention. One or more locking members 126 may be pivotally mounted to the wall portion 102. Pivotally mounted locking members 126 are rotated into position above the implantable device 101 in order to secure the implantable device 101.

Figure 7:
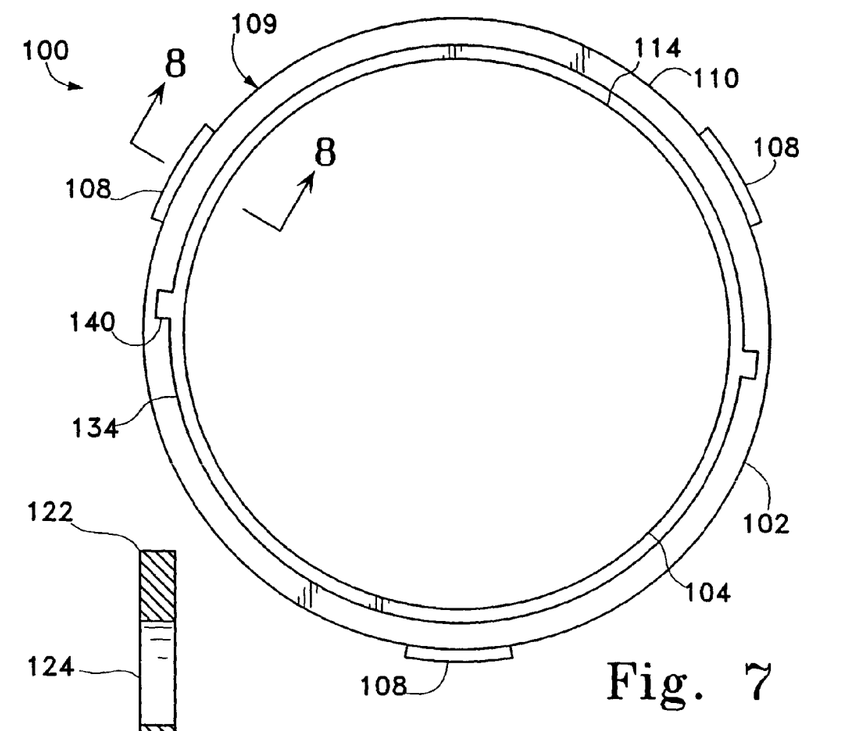
FIG. 7 is a top view of the ferrule according to one variation of the present invention.
Figure 8:
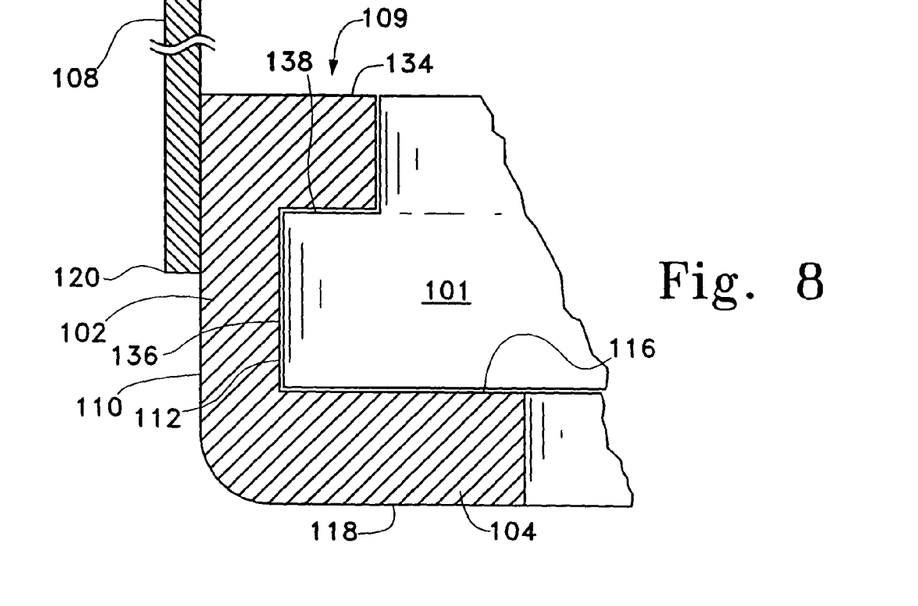
FIG. 8 is a cross-sectional view along line 8—8 of FIG. 7 of the ferrule and implantable device.

Another retainer 109 for removably retaining a self-contained implantable device 101 within the ferrule 100 is shown in FIGS. 7 and 8. The retainer 109 includes a flange 134 that extends inwardly from the inner surface 112 of the wall portion 102 and defines a radial groove 136 dimensioned to receive at least one complementary mating member 138 located on the surface of the implantable device 101. The flange 134 includes receiving notches 140 for receiving the mating member 138 of the implantable device 101 into the radial groove 136. The implantable device 101 is locked to the ferrule 100 by engaging the mating surfaces in a rotate-and-lock fashion. The self-contained implantable device 101 may also be secured within the ferrule 100 employing any combination of retainers discussed above.

The dimensions of the ferrule 100 may be customized from computer tomography (CT) imaging data. Information from CT scans are used to design and dimension a ferrule 100 that matches the opening, contour, and thickness of each patient's cranium in addition to being dimensioned to receive a particular standardized or customized implantable device 101. The ferrule 100 preferably is formed from biologically compatible material such as titanium, tantalum, or titanium alloy. However, the invention is not so limited and any other biologically compatible material may be employed.

Figure 9:
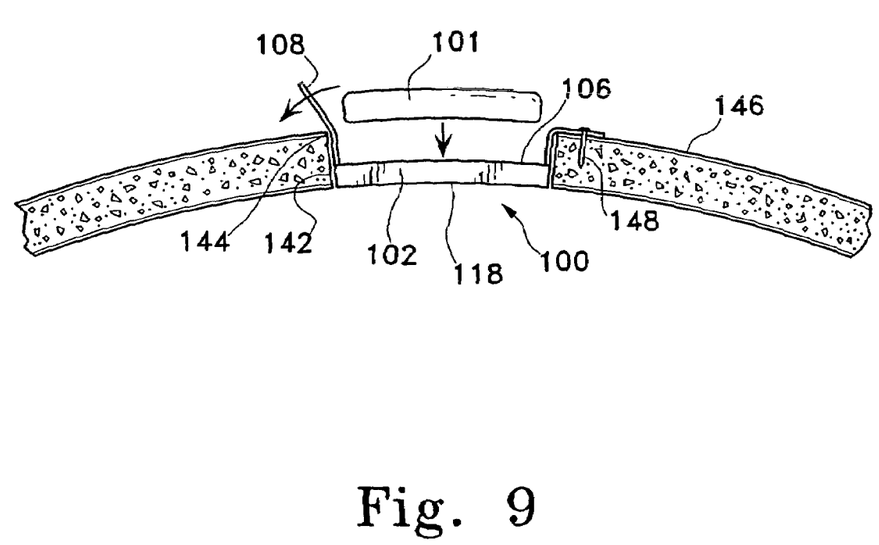
FIG. 9 is sectional view of the ferrule, implantable device, and cranial opening.

As shown in FIG. 9, a cranial opening 142 is formed and the ferrule 100 is surgically positioned within the opening 142. When the ferrule 100 is formed of pliant material, the supporting tabs 108 are capable of being bent over an edge 144 of the cranial opening 142 as shown while the ridge 106 can be designed to provide the necessary structural rigidity for device 101 support. Since the thickness of the patient's skull may vary across the opening in the skull, each of the supporting tabs 108 may have to be bent individually and at different points along each tab 108. Alternatively, the tabs 108 may be formed during manufacture of the ferrule 100 or bent prior to surgery.

After the supporting tabs 108 are bent into position, the ferrule 100 is secured to the patient's cranium 146 with bone screws 148. Self-tapping bone screws 148 of the type used in oral, maxofacial, and cranial surgery are passed through the apertures 124 in the supporting tabs 108 and into the patient's skull 146. The implantable device 101 is then placed and secured within the ferrule 100 and supported in part by the shelf portion 104. If an interlocking flange is employed to secure the implantable device 101 to the ferrule 100, these surfaces are engaged and the device 132 is rotated to lock the device 132 to the ferrule 100. If a locking member 126 is employed, the locking member 126 is positioned atop the device 132 and fixed to the ferrule 100 as discussed above. If a detent portion 127 is employed, the implantable device 101 is positioned beneath the detent portion 127 or the detent portion 127 is bent over the implantable device 101. The detent portion 127 may be secured to the implantable device 101 with screws or the like. Additionally, sutures may be employed to secure the implantable device 101 to the ferrule 100.

Figure 10:
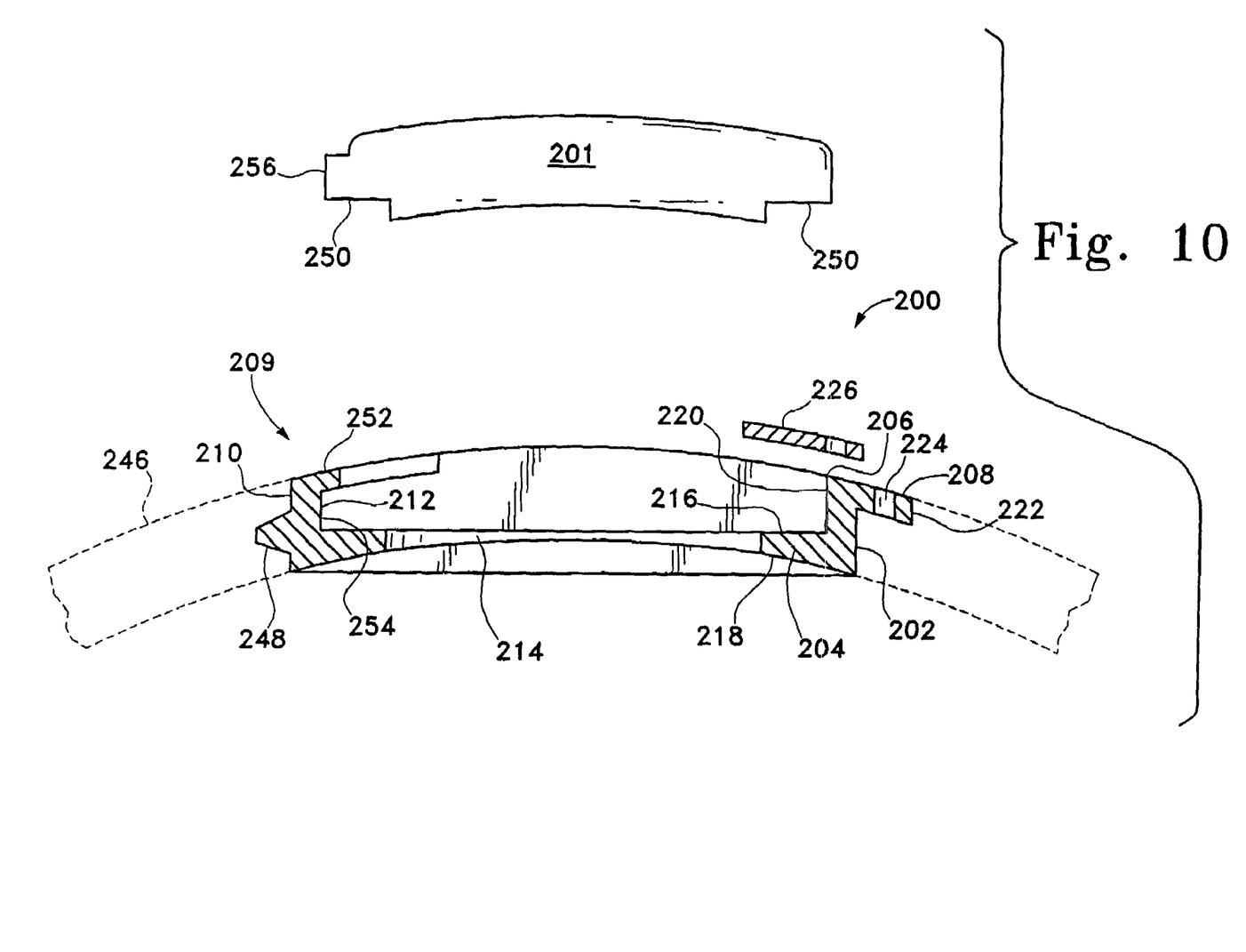
FIG. 10 is a cross-sectional view of the ferrule according to one variation of the present invention, implantable device, and cranial opening.

Referring now to FIG. 10, there is shown another variation of the ferrule 200. The ferrule 200 includes a wall portion 202, a shelf portion 204, a rim 206, at least one supporting tab 208, and a retainer 209 for securing an implantable device 201 within the ferrule 200.

The wall portion 202 encompasses and extends upwardly from the shelf portion 204. The wall portion 202 includes an outer surface 210 and an inner surface 212. Generally, the wall portion 202 has an outer surface 210 that conforms to the cranial opening and an inner surface 212 that is suitable for receiving the implantable device 201. The outer surface 210 of the wall portion 202 of the ferrule 200 shown in FIG. 10 includes an intra-osseous extension 248 that may or may not include holes for osseointegration of the ferrule 200. Although only a singular intra-osseous extension 248 is illustrated, multiple extensions of various shapes may be used. Further, various surface treatments of the outer surface 210 alone or in combination with the extensions may be employed to promote the eventual osseointegration of the ferrule 200 with the bone.

The shelf portion 204 extends inwardly from the inner surface 212 of the wall portion 202 and defines an aperture 214. The shelf portion 204 includes an inner surface 216 and an outer surface 218. The outer surface 218 is generally concave to conform to the natural shape of the brain. The shelf portion 204, in part, supports the implantable device 201. As shown, the inner surface 216 of the shelf portion 204 is generally flat corresponding to the flat portions 250 of the implantable device 201 that contact the inner surface 216 of the shelf portion 204. In general, the inner surface 216 of the shelf portion 204 is adapted to receive a particularly shaped device 201 and the outer surface 218 is generally configured to conform to the curvature of the patient's brain.

The rim 206 encompasses the wall portion 202 and is interrupted by at least one supporting tab 208. The supporting tab 208 includes a proximal end 220 and a distal end 222. The supporting tab 208 is integrally connected to the wall portion 202 relatively near the proximal end 220, and an aperture 224 for receiving a bone screw is defined relatively near the distal end 222. As discussed above, the supporting tab 208 may be formed during manufacture, bent prior to surgery or at the time of implantation of the ferrule 200 by the surgeon.

Another retainer 209 is illustrated in FIG. 10. This retainer 209 is particularly well adapted for the securing an implantable device 201 that is not substantially circular in shape and therefore cannot be rotated and locked into position. In this variation, the retainer 209 includes a flange 252 that extends inwardly from the inner surface 212 and defines a radial groove 254 dimensioned to receive, in a slip-fit engagement, a complimentary mating member 256 located on the implantable device 201. One or more locking members 226 of the type discussed above are also included to help secure the implantable device 201 within the ferrule 200.

After the cranial opening is formed, an additional groove may be formed in the cranium to receive the supporting flange 252 such that the outer surface of the ferrule 200 is even with the outer surface of the patient's cranium. A bore for the insertion of the intra-osseous extension may also be formed. Once positioned within the cranial opening, a bone screw is passed through the aperture 224 in the supporting tab 208 and into the patient's skull 246.

The implantable device 201 is then placed into the ferrule 200 such that the mating member 256 of the implantable device 201 is slipped under the flange 252 of the ferrule 200 to engage the radial groove 254 such that the mating member 256 is positioned within the radial groove 254. The implantable device 201 is then located above the shelf portion 204 such that the implantable device 201 contacts the inner surface 216 of the shelf portion 204. If a locking member 226 is used, it is positioned atop the implantable device 201 and secured. Again, different types of locking members 226 having various shapes may be employed. For example, a locking member 226 that is pivotally mounted to the wall portion 202 may be swiveled over the implantable device 201 and then tightened to lock the device 232 within the ferrule 200. Alternatively, an elongated locking member 226 may extend from the rim 206, cross a portion of the device 232, and return to the rim 206 and be secured to the wall portion 202 via screws. The locking member 226 may additionally be secured to the implantable device 201. The locking member 226 is easily removed enabling removal of the entire implantable device 201 or enabling access for maintenance such as replacement of a battery.

While the present invention has been described with reference to one or more particular variations, those skilled in the art will recognize that many changes may be made thereto without departing from the spirit and scope of the present invention. Each of these embodiments and obvious variations thereof are contemplated as falling within the spirit and scope of the claimed invention, which is set forth in the following claims.

What is claimed is:

1. A ferrule for removably retaining a self-contained implantable device within a cranial opening of a patient comprising:
    a shelf portion having an inner surface and an outer surface, the inner surface of the shelf portion substantially conforming to a self-contained implantable device;
    a wall portion having an inner surface and an outer surface, the wall portion encompassing the shelf portion, the inner surface of the wall portion substantially conforming to the self-contained implantable device, and the outer surface substantially conforming to a cranial opening; and
    at least one supporting tab connected to the wall portion.

2. The ferrule of claim 1 wherein the supporting tab is bendable.

3. The ferrule of claim 1 wherein the supporting tab defines at least one aperture for receiving a bone screw.

4. The ferrule of claim 1 further including at least one intra-osseous extension.

5. The ferrule of claim 1 wherein the outer surface of the shelf portion is generally concave.

6. The ferrule of claim 1 wherein the shelf portion defines an aperture.

7. The ferrule of claim 1 further including a retainer for retaining the implantable device within the ferrule.

8. The ferrule of claim 7 wherein the retainer includes at least one detent portion.

9. The ferrule of claim 7 wherein the retainer includes at least one locking member.

10. The ferrule of claim 9 wherein the locking member is integrally formed with the wall portion.

11. The ferrule of claim 9 wherein the locking member defines at least one aperture.

12. The ferrule of claim 11 wherein the wall portion of the ferrule defines at least one receiving bore corresponding to the aperture in the locking member adapted to secure the locking member to the wall portion.

13. The ferrule of claim 12 wherein at least one of the apertures of the locking member is adapted for securing the locking member to the implantable device.

14. The ferrule of claim 9 wherein the locking member is pivotally mounted to the wall portion.

15. The ferrule of claim 7 wherein the retainer includes a flange extending inwardly from the inner surface of the wall portion, the flange defining a radial groove dimensioned to receive at least one complementary mating member located on the implantable device in a slip-fit engagement.

16. The ferrule of claim 15 wherein the retainer further includes at least one locking member.

17. The ferrule of claim 16 wherein the locking member defines at least one aperture.

18. The ferrule of claim 17 wherein the wall portion of the ferrule defines at least one receiving bore corresponding to the aperture in the locking member adapted to secure the locking member to the wall portion.

19. The ferrule of claim 17 wherein at least one of the apertures of the locking member is adapted for securing the locking member to the implantable device.

20. The ferrule of claim 16 wherein the locking member is pivotally mounted to the wall portion.

21. The ferrule of claim 7 wherein the retainer includes a flange extending inwardly from the inner surface of the wall portion, the flange defining at least one receiving notch and a radial groove dimensioned to receive at least one complementary mating member located on the implantable device in a rotate-and-lock fashion.

22. A method for removably retaining a self-contained implantable device within a cranial opening of a patient, comprising:
    forming a cranial opening;
    providing a ferrule, the ferrule having a shelf portion, the shelf portion having an inner surface and an outer surface, the inner surface of the shelf portion substantially conforming to a self-contained implantable device; the ferrule further having a wall portion having an inner surface and an outer surface, the wall portion encompassing the shelf portion, the inner surface of the wall portion substantially conforming to the self-contained implantable device, and the outer surface substantially conforming to the cranial opening, the ferrule having at least one supporting tab connected to the wall portion;
    inserting the ferrule into the cranial opening;
    fixing the ferrule to the cranium;
    inserting the self-contained implantable device into the ferrule; and
    removably securing the implantable device to the ferrule.

23. The method of claim 22 wherein the step of fixing the ferrule to the cranium includes bending the supporting tab over the cranial opening.

24. The method of claim 22 wherein the step of providing a ferrule includes providing a ferrule wherein the supporting tab defines at least one aperture; the step of fixing the ferrule to the cranium includes passing a bone screw through the aperture in the supporting tab and into the cranium.

25. The method of claim 22 wherein the step of providing a ferrule includes providing a ferrule including at least one intra-osseous extension.

26. The method of claim 22 wherein the step of providing a ferrule includes providing a ferrule having at least one locking member; and the step of removably securing the self-contained implantable device to the ferrule includes positioning the locking member over the implantable device.

27. The method of claim 26 wherein the step of removably securing the self-contained implantable device to the ferrule includes the step of securing the locking member to the wall portion.

28. The method of claim 27 wherein the locking member further includes at least one aperture and the wall portion includes at least one receiving bore corresponding to the aperture in the locking member; the step of securing the locking member to the wall portion includes passing a screw through the aperture in the locking member and into the receiving bore.

29. The method of claim 26 wherein the step of securing the implantable device to the ferrule includes securing the locking member to the implantable device.

30. The method of claim 22 wherein the step of providing a ferrule includes providing a ferrule having a flange extending inwardly from the inner surface of the wall portion, the flange defining a radial groove dimensioned to receive at least one complementary mating member located on the self-contained implantable device.

31. The method of claim 30 wherein the step of inserting the self-contained implantable device into the ferrule includes the steps of:
 positioning the mating member of the self-contained implantable device within the radial groove; and
 locating the self-contained implantable device above the shelf portion such that the device contacts the inner surface of the shelf portion.

32. The method of claim 30 wherein the step of removably securing the self-contained implantable device to the ferrule includes rotating the self-contained implantable device to lock the implantable device within the ferrule.

33. The method of claim 30 wherein the step of providing a ferrule includes providing a ferrule having at least one locking member; the step of securing the self-contained implantable device to the ferrule includes the steps of:
 positioning the locking member above the implantable device; and
 securing the locking member to the wall portion.

34. The method of claim 22 wherein the step of providing a ferrule includes providing a ferrule having at least one detent portion; the step of securing the implantable device to the ferrule includes positioning the implantable device between the shelf portion and the at least one detent portion.

35. A ferrule for removably retaining a self-contained implantable device within a cranial opening of a patient comprising:
 a shelf conforming to a self-contained implantable device, and
 an outer surface adapted to a cranial opening.

36. The ferrule of claim 35 wherein the outer surface is configured to being customized from patient-specific data.

37. The ferrule of claim 36 wherein the patient-specific data is obtained from computer tomography imaging.

38. The ferrule of claim 36 wherein the patient-specific data includes thickness and curvature of the skull.

39. The ferrule of claim 36 wherein the patient-specific data is inputted into computer modeling software.

40. The ferrule of claim 36 wherein the patient-specific data is compared to a first outer shape of the ferrule, the first outer shape of the ferrule being changed to a second outer shape of the ferrule, the second outer shape of the ferrule being adapted to the patient-specific data.

41. A method for removably retaining a self-contained implantable device within a cranial opening of a patient comprising:
 providing a self-contained implantable device; and
 providing a ferrule, the ferrule having a shelf and an outer surface, the shelf of the ferrule adapted to a self-contained implantable device, the outer surface adapted to a cranial opening.

42. The method of claim 41 further including the step of obtaining patient-specific data.

43. The method of claim 41 wherein the step of providing a ferrule further includes the steps of:
 providing a ferrule having a first outer surface;
 comparing the patient-specific data to the first outer surface of the ferrule; and
 changing the first outer surface of the ferrule to a second outer surface of the ferrule such that the second outer surface of the ferrule is adapted to the patient-specific data.

44. The method of claim 41 wherein the step of providing a ferrule further includes the steps of:
 providing a ferrule having a first inner surface;
 comparing the patient-specific data to first inner surface of the ferrule; and
 changing the first inner surface of the ferrule to a second inner surface of the ferrule such that the second inner surface of the ferrule is adapted to the patient-specific data.

45. The method of claim 42 wherein the step of obtaining patient-specific data further includes obtaining patient-specific data using computer tomography imaging.

46. The method of claim 42 wherein the patient-specific data includes skull thickness and curvature.

47. The method of claim 42 further including the step of inputting the patient-specific into computer modeling software.

* * * * *

UNITED STATES PATENT AND TRADEMARK OFFICE
CERTIFICATE OF CORRECTION

PATENT NO.        : 7,158,833 B2
APPLICATION NO.   : 10/639842
DATED             : January 2, 2007
INVENTOR(S)       : Benjamin D. Pless et al.

It is certified that error appears in the above-identified patent and that said Letters Patent is hereby corrected as shown below:

In column 4, replace "from the wall potion 102" with --from the wall portion 102--.

Signed and Sealed this

Twenty-fourth Day of April, 2007

JON W. DUDAS
*Director of the United States Patent and Trademark Office*